United States Patent
Shenfeld et al.

(10) Patent No.: US 6,358,937 B1
(45) Date of Patent: Mar. 19, 2002

(54) METHOD FOR THE TREATMENT OF CANCER USING PHOSPHATIDIC ACID-COMPRISING COMPOSITIONS

(75) Inventors: Avner Shenfeld, Rehovot; Meir Shinitzky, Kfar Shmariyahu, both of (IL)

(73) Assignee: Modus Biological Membranes Ltd., Rehovot (IL)

( * ) Notice: Subject to any disclaimer, the term of this patent is extended or adjusted under 35 U.S.C. 154(b) by 0 days.

(21) Appl. No.: 09/526,730

(22) Filed: Mar. 16, 2000

Related U.S. Application Data (62) Division of application No. 09/171,972, filed as application No. PCT/IL97/00147 on May 6, 1997, now Pat. No. 6,051,564.

(30) Foreign Application Priority Data

May 8, 1996 (IL) .................................................. 118180

(51) Int. Cl.$^7$ .............................................. A61K 31/66
(52) U.S. Cl. ....................................................... 514/120
(58) Field of Search ......................................... 514/120

(56) References Cited

PUBLICATIONS

Moonis M, et al., "Liposomal hamycin in the control of experimental aspergillosis in mice: effect of phosphatidic acid with and without cholesterol." *J. Antimicrob. Chemother.*, vol.31, issue 4, Apr. 1993, pp. 569–79, abstract.
Seydel JK, et al., "Drug membrane interaction and the importance for drug transport, distribution, accumulation, efficacy and resistance." *Arch. Pharm.*, vol.327, issue 10, Oct. 1994, pp. 601–610, abstract.
Hannan SE, et al., "Cigarette smoke alters plasma membrane fluidity of rat alveolar macrophages," *Am. Rev. Respir. Dis.*, vol. 140, issue 6, Dec. 1989, pp. 1668–1673, abstract.
Shinitzky, M., *Physiology of Membrane Fluidity*, vol. 1, CRC Press, Inc., pp. 1–51, 1984.
Heron, D.S., et al., "Alleviation of Drug Withdrawal Symptoms by Treatment with a Potent Mixture of Natural Lipds" *Eur. J. Pharmacology*, vol. 83, 1982, pp. 253–261.
Crews, F.T., et al., "Changes in Cortical Synaptosomal Plasma Membrane Fluidity and Composition in Ethanol–Dependent Rats," *Psycho–pharmacology*, vol. 81, 1983, pp. 208–213.
Antonian, L., et al., "AL721, A Novel Membrane Fluidizer", *Neuroscience & Biobehavioral Rev.*, vol. 11, Aug. 24, 1987, pp. 399–413.
Mingeot–Leclercq, M.P., et al., "Effect of Acidic Phospholipids on the Acitvity of Lysosomal Phospholipases and on Their Inhibition by Aminoglycoside Antibiotics–I", *Biochemical Pharmacology*, vol. 40, No. 3, 1990, pp. 489–497.
Harris, R.A., et al., "Relationship of Membrane Physical Properties to Alcohol Dependence in Mice Selected for Genetic Differences in Alcohol Withdrawal," *Life Sciences*, vol. 35, No. 26, 1984, pp. 2601–2608.

*Primary Examiner*—Rebecca Cook
(74) *Attorney, Agent, or Firm*—Nath & Associates PLLC; Gary M. Nath; Jerald L. Meyer (57) ABSTRACT

A lipid preparation comprising at least about 10% phosphatidic acid (PA) is used to treat human conditions or disease. Examples of such conditions or disease are withdrawal syndromes or cancer.

5 Claims, 7 Drawing Sheets

METHOD FOR THE TREATMENT OF CANCER USING PHOSPHATIDIC ACID-COMPRISING COMPOSITIONS

This is a division of Ser. No. 09/171,972 filed Feb. 24, 1999, now U.S. Pat. No. 6,051,564 which is a 371 of PCT/IL97/00147 filed May 6, 1997.

FIELD OF THE INVENTION

The present invention concerns lipid-based compositions and use of such compositions in the treatment of withdrawal syndromes or cancer.

BACKGROUND OF THE INVENTION AND PRIOR ART

Withdrawal syndromes can occur during rehabilitation from addiction to drugs, alcohol, cigarettes and from an abrupt decline in the level of various hormones such as that occurring in menopause women. It is expressed in symptoms of seizures, sweat, tremor, nausea, depression, increase in rate of heart beat and in blood pressure, and others. Typically such addiction is treated by a "wash out" period in which the dependency is gradually removed with or without drug intervention. This process is painful and tedious and candidates are thus very often discouraged from entering it. There is thus a strong need for a solution that can ease the difficult period of withdrawal and that would allow people to return to normal life without much complications.

A basic biochemical phenomenon shared by most of the withdrawal syndromes is a change in the composition and in the structure of neuronal cell membranes which is expressed in membrane "fluidity" (Hannan, *Am. Rev. Respir. Dis.*, 140 (1989), 1668–73; Crews, *Psycho-pharmacology*, 81 (1983), 208–13; Harris, *Life Sci.*, 35 (1984), 2601–8; Heron et al., *Eur. J. Pharmacol.*, 83 (1982), 253–261). These changes can at times be counteracted by administration of special natural preparations, resulting in the reduction of the symptoms related to the withdrawal processes (Heron et al., *Eur. J. Pharmacol.*, 83 (1982) 253–261; Shinitzky, *Physiology of membrane fluidity*, (1984), Vol 1, Chapt. 1).

Multi-drug resistance (MDR) is also related to change in the fluidity of the cell membrane (Seydel et al. *Arch. Pharm.*, 327, 601–610, 1994). MDR is a major cause of failure of cancer therapy involving use of cytotoxic drugs, particularly in recurring cancer.

Phosphatidic acid (PA) is a natural phospholipid found in plants and animal tissues. Its content usually does not exceed 5% of the total phospholipids in any of these sources. Therefore, lipid extracts available for human consumption (e.g., soybean phospholipids) are low in PA. Other sources of processed lipid mixtures for per os consumption or intravenous injection are devoid of PA. These include AL 721 (Antonian et al., *Neurosci. Biobehav. Rev.* 11 (1987), 399–413); Bros™ (Fidia Sp. A. Abano-Terme, Italy) or Intralipid™ (Vitrum Inc., Stockholm, Sweden).

Enzymatic procedures utilizing the enzyme phospholipase D for the hydrolysis of phospholipids to PA are known (Waite, M. Ed. The phospholipases, Plenum Press, N.Y., 1987). However, hitherto no use of such procedures to enrich natural lipase preparations with PA has been made. PA incorporated in a liposome containing phosphatidyl choline preparation was shown to reduce toxicity and enhance anti-fungal activity of the anti-fungal drug Hamycin. It was shown that PA had a strong protective effect and increased the survival of mice by 90% after seven days of therapy, as compared to mice treated with Hamycin alone (Moonis M. et al., *J. Anti. Microb. Chemother.*, 31:569–579, 1993). Furthermore, a liposome preparation comprising PA was shown to counter symptoms of kidney toxicity caused by amino glucoside antibiotics as demonstrated by a recuperation in the kidneys' phosphatase activity (Mingert-Leclercq. M.P., et al., *Biochem. Pharmacol.*, 40:489–497, 1990).

GLOSSARY

The following is the meaning of some terms of which use will be made in the text below:

Withdrawal syndrome—a syndrome which is a result of deprivation of the body of a substance to which the body was exposed continuously over a period of time. Such a substance may be an exogenous substance, taken by the individual or may be an endogenous one. Exogenous substances may include, for example, drugs of abuse, e.g. heroin, cocaine, morphine, and others; a variety of therapeutic drugs, e.g. sedatives; tobacco, alcohol, and others. Endogenous substances may include a variety of hormones, particularly such hormones the level of which changes at a certain age. Typical examples of withdrawal syndromes are such that occur in addicts during rehabilitation from addiction to drugs, alcohol, tobacco and other exogenous factors. Another example is that occurring in menopausal women, resulting from change in hormonal level during the menopause.

Withdrawal symptoms—symptoms appearing in an individual having a withdrawal syndrome. Examples are nausea, sweating, shaking, and substance craving, in drug of abuse associated withdrawal syndromes; hot flushes in menopausal women, etc.

PA-enriched lipid preparation (PA-E-LP)—a lipid preparation comprising at least 10% (w/w) of PA, preferably above about 10% and typically within the range of about 20%–75% of PA, out of the total lipid content of the composition.

Natural PA-E-LP—a PA-E-LP derived from it natural lipid preparation, e.g. a phospholipid preparation derived from plants, from animal tissue, or any combination thereof. Such a natural phospholipid preparation may typically be derived from soybean, from egg yolk or from animal sera. The natural PA-E-LP is prepared from a natural phospholipid preparation, typically by an enzymatic process. In a natural PA-E-LP, the remainder of the lipids consist primarily of phospholipids although small quantities, e.g. 0.1–10%, of other lipophilic substances, such as cholesterol, fatty acids, etc., may also be included in the preparation.

GENERAL DESCRIPTION OF THE INVENTION

In accordance with the invention, a natural PA-E-LP was prepared by an enzymatic process. Such a natural PA-E-LP constitutes one aspect of the invention.

In accordance with the invention it was also discovered that PA-E-LP, and particularly natural PA-E-LP, is effective in the treatment of certain human conditions. It was furthermore surprisingly found in accordance with the invention, that PA-E-LP, and particularly natural PA-E-LP is effective in increasing the fluidity of cell membranes and countering various symptoms associated with or involving changes in membranes' fluidity, such as withdrawal symptoms or treatment intended to sensitize MDR resistant cancer cells.

The present invention thus provides by one of its aspects a lipid preparation derived from a natural source enriched to comprise at least about 10% PA, preferably at least about 20% PA and most desirably above 50% PA. Typically, the concentration of PA as a total lipid ingredient, would not exceed 75%.

The concentration given above and below as "%" means to denote the number of weight units of an ingredient per 100 weight units of the entire composition (w/w).

The natural PA-E-LP is preferably obtained from a natural phospholipid preparation by enzymatic treatment using, a synthetic or natural source comprising the enzyme phospholipase-D. The natural phospholipid preparation may be of vegetable origin, may be of animal origin, or a combination thereof. Typical examples of natural phospholipid preparations useful for the preparation of natural PA-E-LP of the invention are, soya lecithin, egg yolk and phospholipids from animal serum. Examples of phospholipase-D sources, are peanuts, typically ground peanuts or a phospholipase-D fraction derived therefrom. Phospholipase-D or a phospholipase-D source is added in an amount and for a time sufficient to hydrolyze at least about 10% or preferably about 25% and most preferably about 50% of the phospholipids to yield PA-E-LP.

By another aspect of the present invention there are provided pharmaceutical compositions comprising PA-E-LP as the active ingredient. Particularly preferred are such compositions comprising natural PA-E-LP as the active ingredient. Examples are pharmaceutical compositions for use in reducing withdrawal symptoms; pharmaceutical compositions for use within the framework of cancer treatment to increase sensitivity of cancer cells, particularly such cells possessing MDR properties, to cytotoxic drugs; etc.

Also provided in accordance with the invention is a method for the treatment of a human condition or disease comprising administering to a patient in need, an effective amount of PA-E-LP.

The term "effective amount" should be understood as in amount of an ingredient sufficient to yield a desired therapeutic effect. For example, within the framework of the treatment of withdrawal syndromes, an effective amount will be an amount which gives rise to permanent or temporary alleviation of withdrawal symptoms in individual, alleviation being either reduction of intensity of withdrawal symptoms or reduction in the rate of appearance of such symptoms, or generally improvement in any parameter characteristic of such withdrawal symptoms. In the case of anti-cancer treatment, an effective amount is an amount giving rise to increased sensitivity of the tumor cells toward cytotoxic drugs, as determined for example by a decrease in the size of a tumor mass.

The pharmaceutical composition of the invention may typically be orally administered although it may also be formulated for topical or parenteral administration. For oral administration the composition may comprise various flavoring agents, edible colors, etc. Furthermore the composition for oral use may also be encapsulated, e.g. in an enterocoated gelatine capsule.

For parenteral administration the composition will typically be injected intravenously (I.V.). Such a parenteral composition may for example comprise soybean multi-triglycerides, egg phospholipids, PA prepared in accordance with the invention, glycerol and distilled water.

A topical composition may be in the form of a gel or a salve and may thus comprise various additives known per se to allow the compositions to obtain such a physical form (e.g. a gelating agent).

The compositions may be used for the treatment of a variety of human conditions and diseases. One preferred embodiment of the invention is concerned with the treatment of withdrawal syndromes. The treatment may be manifested by a permanent improvement in an individual's condition, e.g. the disappearance or reduction of intensity of the withdrawal symptoms, or a temporary disappearance or reduction of such symptoms during an attack.

Withdrawal syndromes which can he treated in accordance with the invention include treatment of menopausal women, particularly treating such women to reduce the occurrence of hot-flushes during the menopausal period; treatment of withdrawal syndrome during rehabilitation from smoking or drug or alcohol addiction; etc.

Another preferred embodiment of the invention is concerned with the treatment of cancer, particularly such related with acquired multi-drug resistance MDR. Development of MDR is a reaction of tumor cells to continuous exposure to cytotoxic agents both in vitro and in vivo. This mechanism is believed to be responsible for the resistance developed by cancer patients to chemotherapy treatment which is currently one of the most serious problems in cancer treatment. It has been shown that the sensitivity of tumor cells to various cytotoxic drugs is correlated with their potency for membrane fluidization. Treatment with the composition of the invention may increase the fluidity of the membrane of tumor cells present in an individual, thereby reversing their acquired multi-drug resistance to various cytotoxic drugs and thus enabling continuation of a chemotherapy regimen, which may result in the improvement of the treated individual's condition.

The invention will now be illustrated in the following examples with occasional reference to the annexed drawings.

EXAMPLE 1

Preparation of PA Mixture (a) Preparation of a Reaction Product

Figure 1:
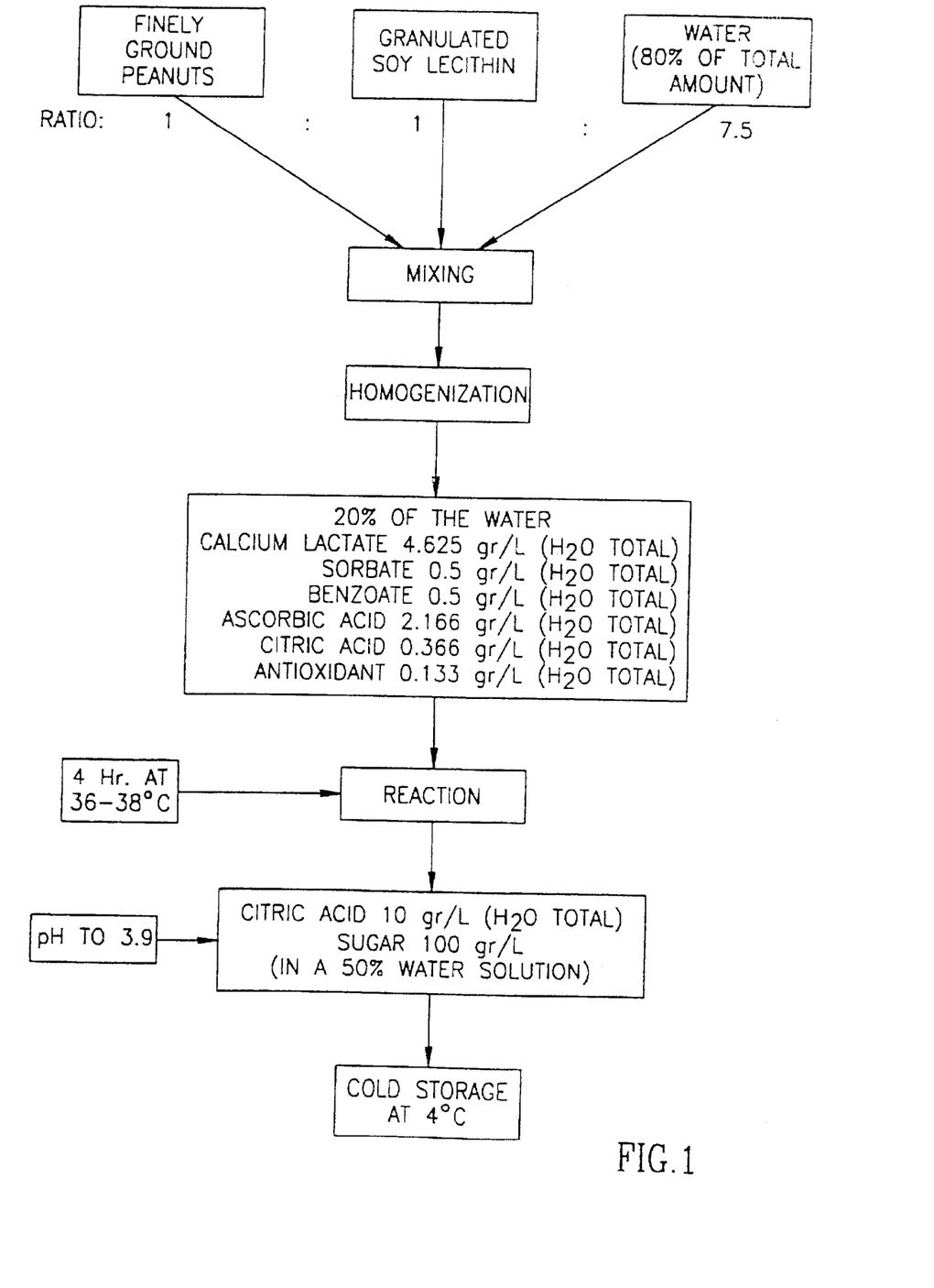
FIG. 1 is a schematic representation depicting the preparation of the PA enriched mixture of the invention. As can be seen in the figure, the ratio of the starting materials (peanuts, soya lecithin and water) is 1:1:7.5, respectively.

FIG. 1 schematically depicts the method of preparation of a PA mixture in accordance with the invention. As can be seen, the starting materials are the following (the amounts calculated in the Example are for a 1l mixture):

1. 150 grams of grained fresh peanuts as an origin of Phospholipase D.
2. 150 grams of granulated soy lecithin as an origin of soybean phospholipids.
3. 1000 ml. to be added to $H_2O$.

The above-mentioned starting materials were mixed in a meat blender, brought to homogenization and then the pH of the mixture was adjusted to a pH of 5.3–5.4 by the addition of calcium lactate, sorbate, benzoate, ascorbic acid, citric acid and an anti-oxidant (each in the amount described in the figure). The mixture was then reacted under continuous mixing for four hours at 36–38° C. after which the pH was once more adjusted to a pH of 3.9 by the addition of citric acid and sugar in amounts described in the figure. The mixture was then stored at 4° C. overnight.

(b) Separation of the Lipid Fraction

Figure 2:
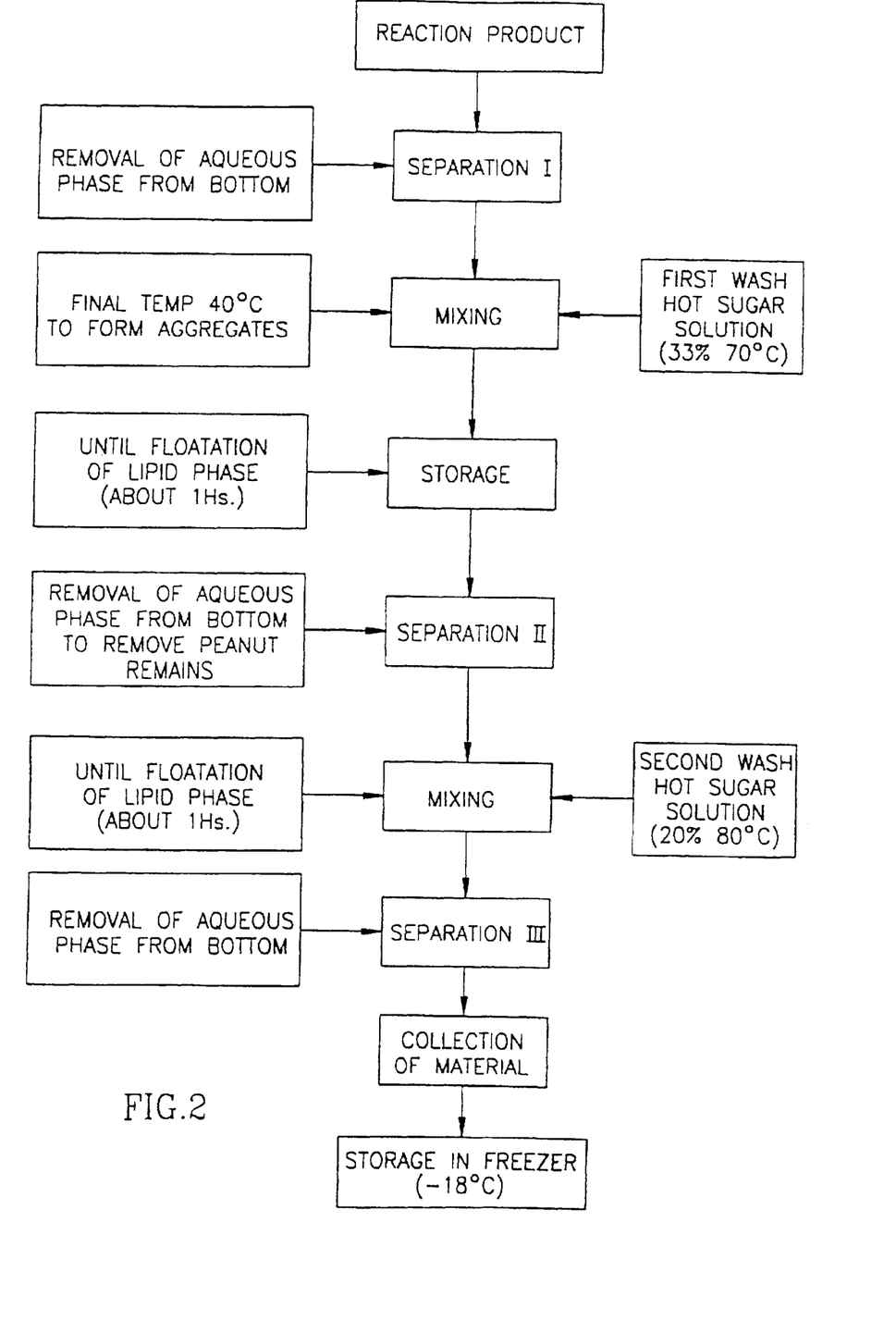
FIG. 2 is a schematic representation depicting the separation of the lipid phase of the PA-mixture prepared by the reaction showed in FIG. 1.

The reaction mixture obtained by the above procedure was then further separated by a procedure depicted schematically in FIG. 2. As seen in the figure, the reaction product was subjected to three main separations (indicated as separations I, II and III in the figure) wherein, generally, in each separation the aqueous phase of the mixture was removed from the bottom until, finally, the separated lipid phase was collected and stored in a freezer (−18° C.).

(c) Preparation of the Lipid Composition for Filling Containers

Figure 3:
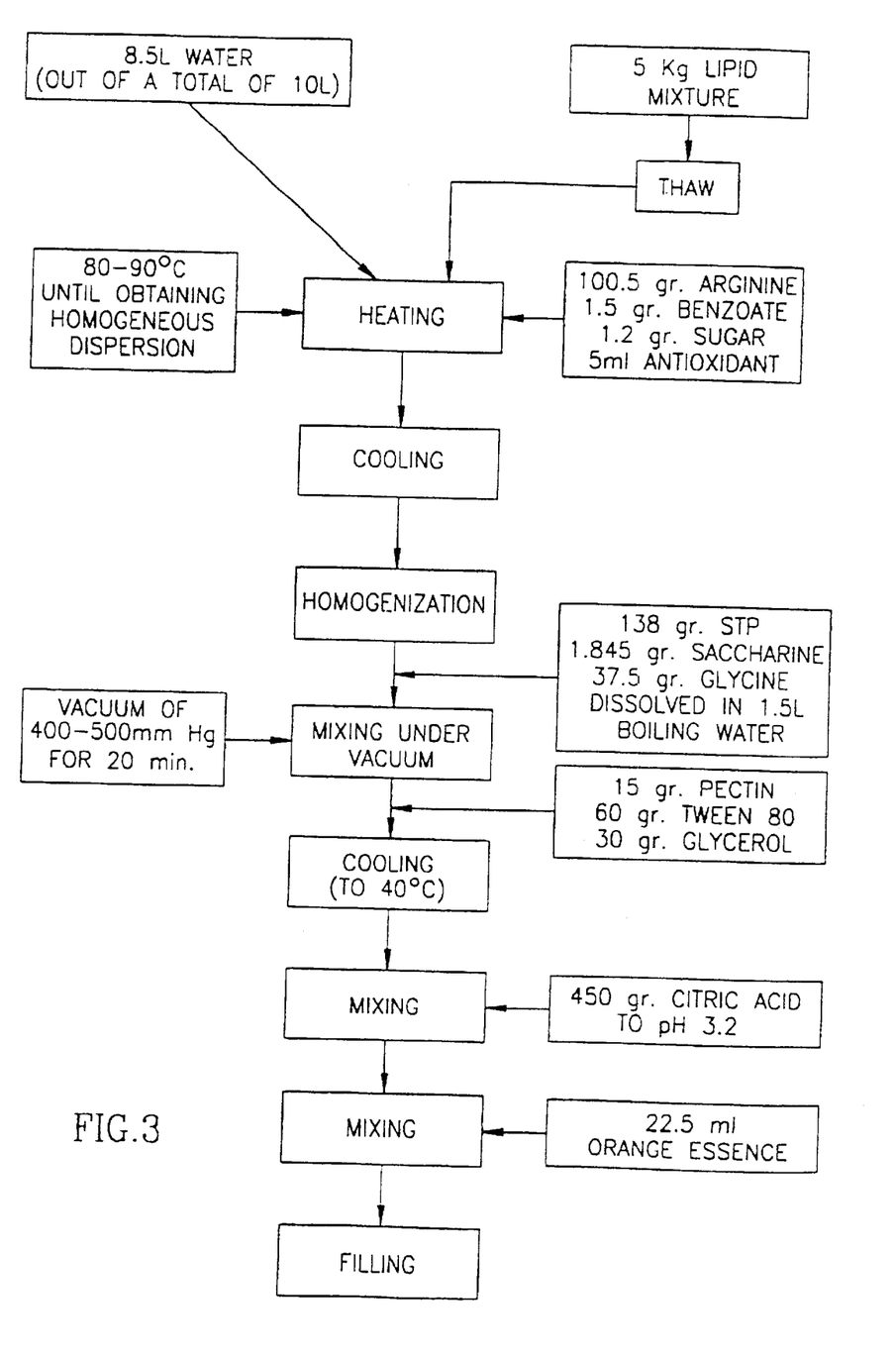
FIG. 3 is a schematic representation depicting the preparation of the PA-mixture of the invention prepared as described in FIGS. 1 and 2 in a suitable form for filling containers.

The lipid mixture obtained by the above separation was subjected to several additional procedures by which it was prepared for filling containers. As seen in FIG. 3, the lipid mixture obtained by the above separation process was first thawed and then treated by heating, cooling, homogenization and mixing as described in FIG. 3 to form a composition suitable for filling containers. The containers are then stored at 4° C. Typically, the size of the containers is such which accommodates half a liter of the mixture.

(d) Preparation of PA Containing Tables

Figure 4:
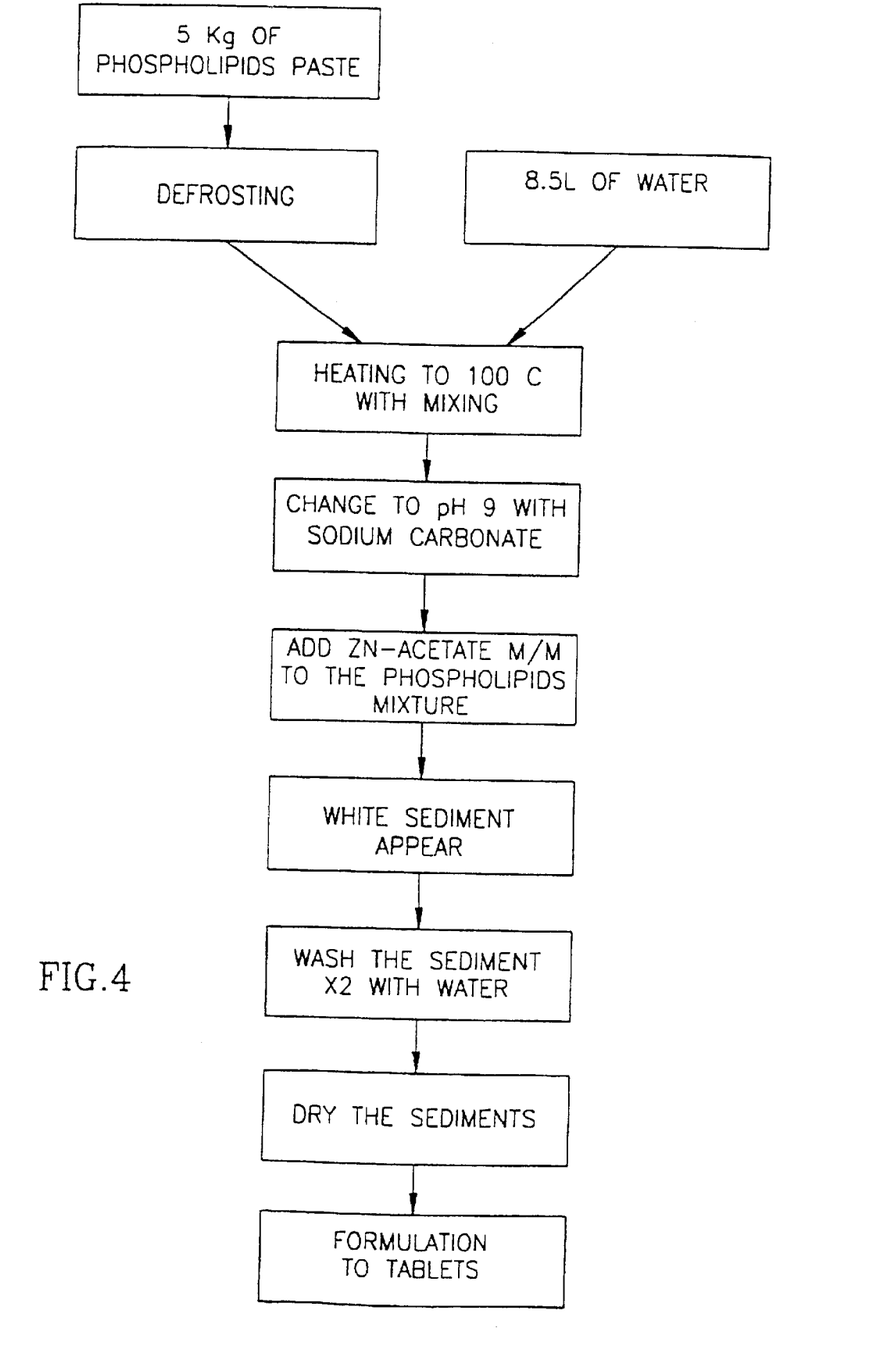
FIG. 4 is a schematic representation depicting the preparation of tablets from the PA-mixture prepared as described in FIGS. 1 and 2.

The PA mixture obtained by the method described in Examples 1(a)-1(c) above and shown in FIGS. 1–3 may also be processed into tablets. The method for preparation of tablets comprising the PA mixture is shown in FIG. 4. As seen in the figure, generally the phospholipid paste obtained by the above process was first defrosted and then heated and the pH of the mixture adjusted to a high pH of about 9. Following addition of zinc acetate to the mixture a white sediment appeared which, after washing and drying, was formulated into tablets.

(e) Profile of PA Formation

Figure 5:
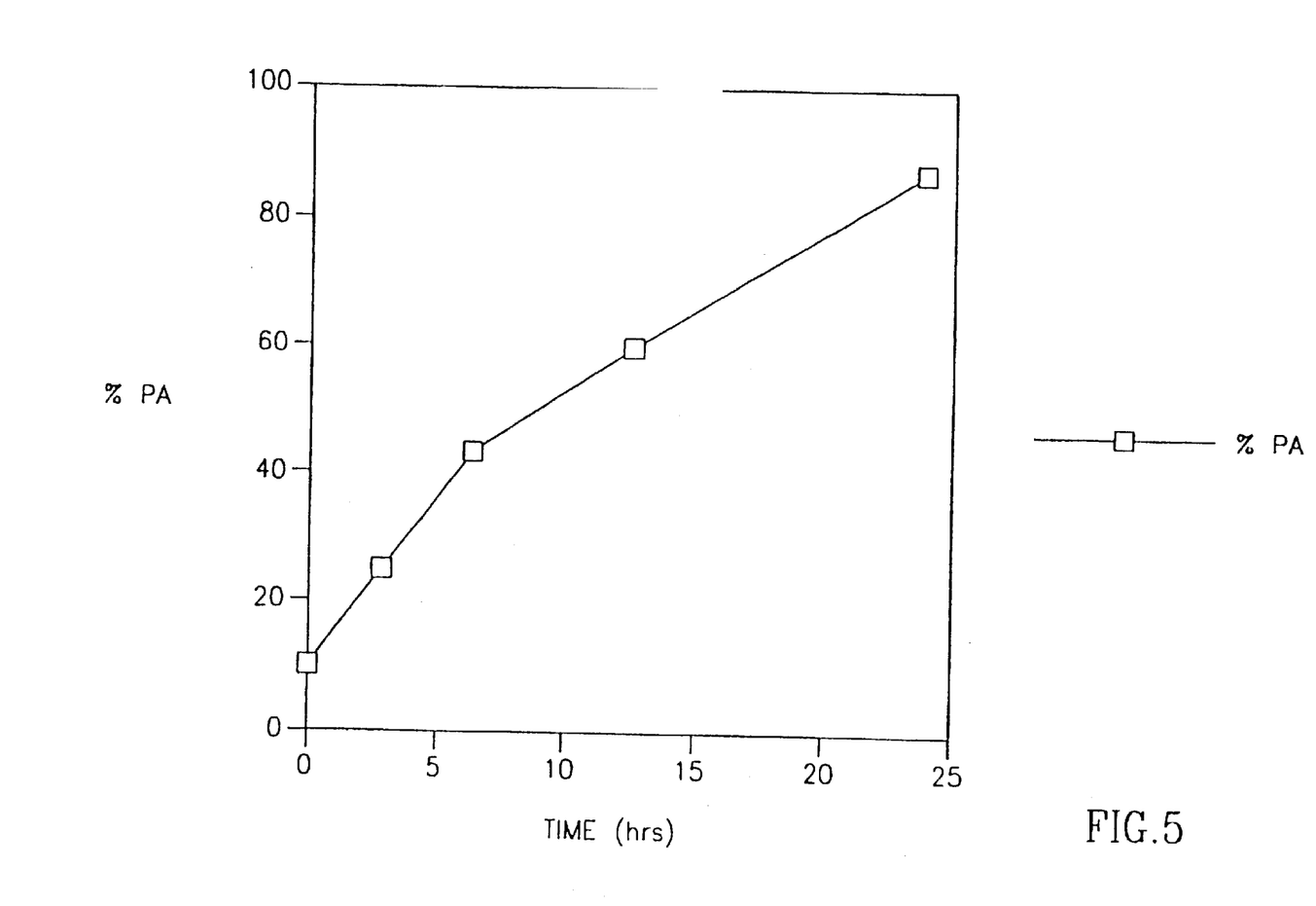
FIG. 5 shows the formation profile of PA during an enzymatic hydrolysis of soybean phospholipids. (The results are present as % from the entire composition).

The profile of formation of PA is depicted in FIG. 5. As can be seen, after about 24 hours, more than 80% of the soybean phospholipid was hydrolyzed yielding a PA enriched preparation.

EXAMPLE 2

The Effect of Phosphatidic Acid (PA) on Lipid Viscosity of Human Lymphocyte Membranes Human lymphocytes ($3 \times 10^6$/ml) from 10 healthy individuals were incubated with 1 mg/ml of 4 different phospholipid preparations and 1 control preparation (phosphate buffered saline-PBS).

Figure 6:
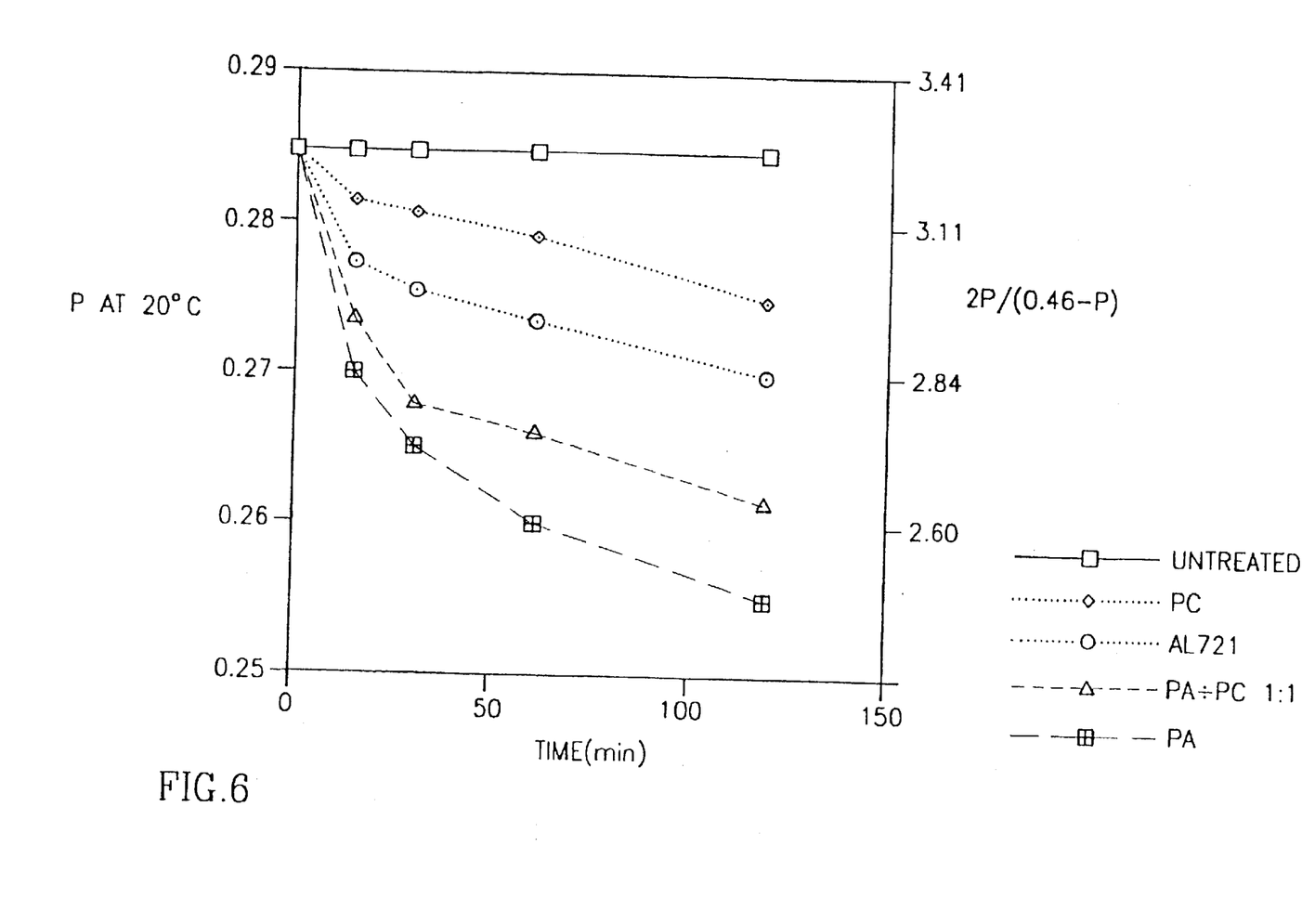
FIG. 6 shows the effect of PA on lipid viscosity of human lymphocytes. The results are presented as the degree of fluorescence polarization P of DPH in the membranes of the washed lymphocytes and are translated to 2P/(0.46-P), which is a linear scale of lipid viscosity (Shinitzky and Barenholtz, *Biochem, Biophys. Acta.* 515, (1978), 367–394). (PC—phosphatidylcholine from egg yolk; AL721—a mixture of triglycerides, PC and phosphatidylethanolamino (PE) from egg yolk; PA—phosphatidic acid obtained by enzymatic reaction of soybean phospholipids; PA+egg PC 1:1—a mixture of PA and PC in equal proportions (by weight)).

The results depicted in FIG. 6 demonstrate the effect of PA in decreasing membrane viscosity (i.e. increasing cell membrane fluidity). It can be seen that at all times, the effect of PA above or in a 1:1 mixture with PC was much stronger than the two other tested preparations.

EXAMPLE 3

Treatment of Menopause Women with a 50% Lipid Mixture

Three groups, each consisting of 10 women over 50 who suffered from hot flushes syndrome, participated in the study. Group A continued routine life without treatment. Group B consumed 12 g of 50% PA lipid mixture (prepared as in Example 1) dispersed in 50 ml of water before breakfast for 40 days. Group C similarly received 24 g of the 50% PA rich lipid mixture in 100 ml of water for 40 days. Each of the participants in Group A, B and C was asked to record the number and intensity level of their daily hot flushes from day 3 to day 40 of the experiment. Participants of Group C were asked to determine these parameters for 3 days one month after termination of the trial (Group D). The results are presented in Table 1 below:

TABLE 1

Daily number of mild, moderate and severe levels of hot flushes (average ± S.D.):

| Group | Mild | Moderate | Severe | Total | Weighted |
|---|---|---|---|---|---|
| A | 0.75 ± 0.9 | 5.0 ± 4.7 | 10.5 ± 3.1 | 16.3 ± 6.2 | 42.3 ± 15.5 |
| B | 3.50 ± 3.3 | 2.5 ± 4.3 | 2.5 ± 4.3 | 8.5 ± 2.3 | 16.0 ± 9.0 |
| C | 3.50 ± 2.5 | 1.5 ± 0.7 | 2.3 ± 3.8 | 7.3 ± 1.0 | 13.4 ± 10.0 |
| D | 2.50 ± 3.7 | 4.8 ± 5.5 | 4.2 ± 5.6 | 11.5 ± 2.4 | 24.7 ± 11.0 |

A—Control
B—12 g of lipid formulation per day
C—24 g of lipid formulation per day
D—One month after termination of medication in Group C.

EXAMPLE 4

Alleviation of Morphine Withdrawal Symptoms by 50% PA Rich Lipid Mixture

Experiments were carried out as outlined in Heron et al., *Eup. J. Pharmacol.*, 83, (1982), 253–261. Two groups of 20 mice each were injected subcutaneously twice daily with morphine HCl solution (10 mg/ml) in saline up to 100 mg/kg for 9 days, or with saline alone (control). The treated group was divided into two sub-groups each receiving a 6% lipid diet. One group of mice received corn oil and the other a PA rich diet (the PA preparation prepared as in Example 1). The withdrawal syndromes were induced by injection (i.p.) with naloxone (2.5 mg/kg), and then recorded for a period of 25 min in a blind mode.

The results, shown in Table 2 below, demonstrate that PA had a very strong reducing effect on the mices' withdrawal symptoms.

TABLE 2

Alleviation of morphine withdrawal symptoms by 50% PA rich lipid mixture

| Symptoms | Purina-chaw diet + 6% corn oil (control group) | Purina-chaw diet + 6% PA lipid mixture |
| --- | --- | --- |
| 1. Jumps | 32 ± 10 | 5 ± 0.6 |
| 2. Body shakes | 15 ± 4 | 6 ± 2 |
| 3. Forelimb tremor | <50% | >20% |

Jumps - Number of jumps per 25 min.
Body shakes - Number of body shakes per 25 min.
Forelimb tremor - Precent of animals showing continuous and strong tremor of forelimbs (more than 70 episodes in 25 min). Control groups were void of any behavioral abnormalities.

EXAMPLE 5
Alleviation of Smoking Withdrawal Symptoms by 50% PA Enriched Lipid Mixture 37 chronic smokers of 20–40 cigarettes per day (CPD) formed the experimental group for testing the effect of the PA lipid mixture of the invention on withdrawal symptoms associated with smoking cessation. The prerequisites for admission to the experiment were:

(a) willingness of the subject to stop cigarette smoking;

(b) self-confessed inability to stop smoking without external assistance.

Initially, the subjects volunteered for the study were divided at random into two equal groups: subjects of the first group receiving a one daily dose of the 50% PA mixture (prepared as described in Example 1 above) and subjects of the second group (control group) receiving a one daily dose of a non-active preparation. However, due to abandonment of several of the subjects at the beginning of the study as well as the striking off of results of several other subjects who completed the study but did not diminish their rate of smoking at all, the remaining 37 subjects were divided into the two above groups as shown in Table 3 below:

TABLE 3

| | PA-preparation | Non-active preparation | Total |
| --- | --- | --- | --- |
| Male | 8 | 13 | 21 |
| Female | 10 | 6 | 16 |
| Total | 18 | 19 | 37 |

The subjects received either the PA mixture or the non-active mixture over a period of one month.

The following six parameters were studied throughout the study:

(a) Parameters for Evaluating Smoking Heaviness

(i) number of cigarettes smoked per day;

(ii) time between waking and smoking the first cigarette; and

(iii) difficulty of refraining from smoking in public places.

The above three parameters were tested at day 0 of the study, at day 7 and at day 21 of the study.

(b) Parameters for Evaluating the Severity of Withdrawal Symptoms

(i) disquiet;

(ii) extra appetite; and

(iii) need to smoke.

The above parameters were tested at day 7 of the study and on day 21 of the study. Various blood parameters of each of the subjects were also evaluated (including a complete blood count evaluation of sub populations of T-cell, B-cell and NK cell numbers and evaluation of intracellular cytokines) at day 0 of the study as well as at the end of three weeks of the study.

All the parameters were scored on a 0–4 scale (expressed finally on a scale of 1–5 respectively since some tests did not accept 0 as a parameter).

By using logistic regression statistical analysis, it was decided that the indicative parameters in the test would be the number of cigarettes smoked by a subject per day at the end of week three (day 21) of the study and the desire to smoke expressed by the same subject on the same day. A comparison was made to assess whether subjects treated by the PA-mixture smoked less at the end of week three of the experiment as compared to subjects of the control group receiving the non-active mixture and whether subjects of the above first group also had less craving for smoking at the end of week 3 of the study as compared to subjects of the above control group.

Results

Figure 7:
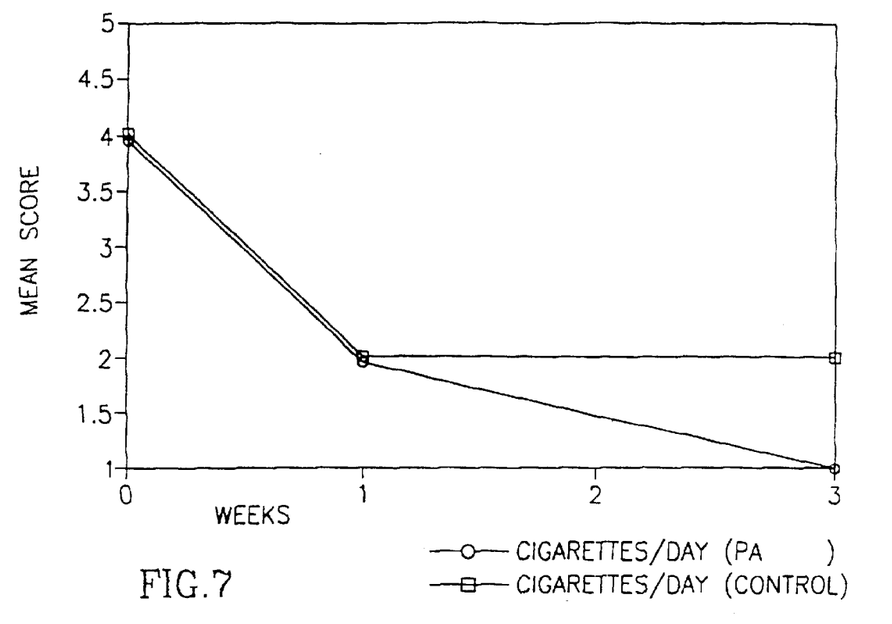
FIG. 7 is a graphic representation depicting the mean number of cigarettes smoked by subjects participating in a study assessing the affect of the PA-mixture of the invention on smoking withdrawal symptoms (See Example 5). The number of cigarettes smoked per day by subjects of the treatment group (treated with the PA-mixture of the invention) was compared to the number of cigarettes smoked by subjects of the control group (receiving a non-active mixture) at different time periods after the beginning of the study. The number of cigarettes is expressed by a mean score calculated as explained in Example 5.

Statistical analysis of the results using Students Test and Mann-Whitney's U test of the above study showed the following:

1. As seen in FIG. 7, the number of cigarettes smoked per day at the end of week 3 of the study was significantly smaller in subjects of the group treated with the PA-mixture as compared to that of subjects of the control group ($\alpha<0.05$).

Figure 8:
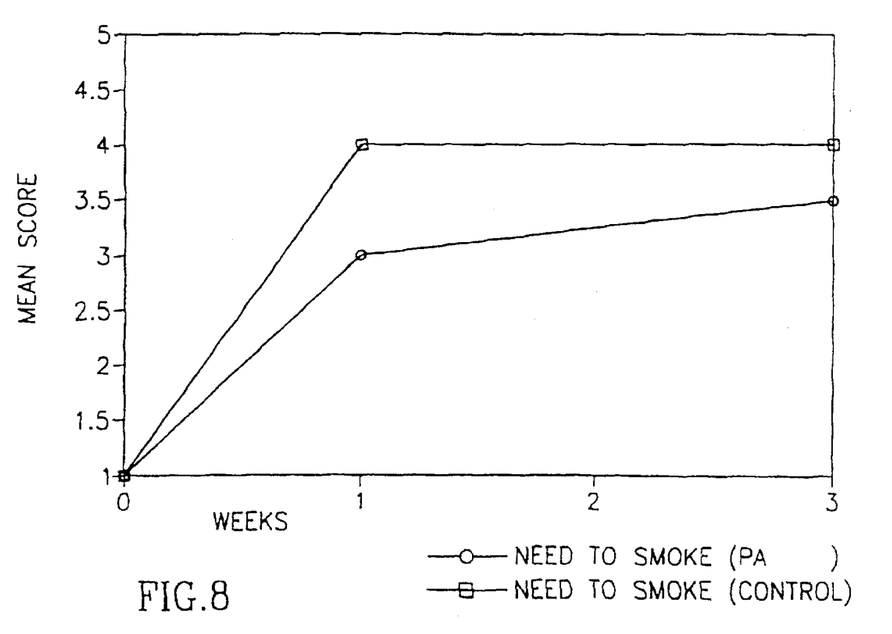
FIG. 8 is a graphic representation showing the need to smoke of subjects participating in a study assessing the affect of the PA-mixture of the invention on smoking withdrawal symptoms (Example 5). The need to smoke of subjects in the treatment group (receiving daily treatment with the PA-mixture of the invention) was compared to that of subjects of the control group (receiving non-active mixtures daily) at different times after the beginning of the study.

2. Statistical analysis showed that due to the fact that the tendencies of the unrelated tested samples were non-normal and the variances of the two compared groups was unequal, the statistical analysis should be performed by Kolmogorov-Smirnov's test. According to this test, and as seen in FIG. 8, the desire of subjects of the group grated by the PA-mixture at the end of three weeks of the study is significantly smaller than that of subjects of the control group ($\alpha$ smaller than 0.05).

EXAMPLE 6
Alleviation of Alcohol Withdrawal Symptoms by 50% PA Rich Lipid Mixture Volunteers for this study are alcohol addicts at the age of 25–65 which are defined in the clinic as "alcoholics" which frequently become "drunks". The above two terms "alcoholics" and "drunks" are used in accordance with the definitions provided by the World Health Organization 1951 which are used until today (Jelinek, E.M., *The Disease Concept of Alcoholism* New Haven, Hill House Press, 1960 and Hamburg S., "Alcohol Withdrawal in Family and Community" (In Hebrew), 1976, respectively).

The following parameters are tested at the beginning of the study and at its end:

(a) Independent Parameters

(i) personal data;

(ii) demographic, socio-economic and health data; and

(iii) characterization of addiction habits (quantitative and qualitative).

Suitable volunteers are such that are addicted to alcohol (which is not table wine or beer) and which have expressed their desire to withdraw from drinking. Subjects are people who are active at work, do not suffer from other chronic illnesses or from neurological or psychiatric disorders besides the addiction. In addition, subjects are not addicted to drugs and do not take psychiatric medicines regularly. Furthermore, all subjects are people that have a supportive family that can also be questioned as to the changes which the subject undergoes during the study.

(b) Dependent Parameters
 (i) physiological changes: pulse, blood pressure, sensitivity to vibrations, capability of carrying out gentle actions, overview of calorie intake which is not from alcohol;
 (ii) level of functioning in accordance with the following parameters:
  (a) home and social functioning hours;
  (b) hours in which subject is disconnected homewise and socially;
  (c) coping with financial matters;
  (d) quality of partnership in a family load.
 (iii) an effective evaluation is carried out with the aid of a questionnaire before and after treatment. Subjects in the study are divided into two groups:
  (1) subjects receiving a syrup comprising the PA-mixture of the invention twice a day for a month;
  (2) subjects receiving the syrup without the PA-mixture twice a day for a month.

The above-mentioned dependent and independent parameters of the subjects of above group (a) (treatment group) are compared to the same parameters of subjects of the above group (b) (control group) at the beginning of the study and at its end (after one month).

EXAMPLE 7
Membrane Fluidity of Drug Resistance Cell Lines Treated with Phospholipid Acid (PA) and Soy Phospholipids (SP)

Resistant cell lines were developed as described by Ramu et al. (*Cancer Chemother. Pharmacol.,* 515, 367–394, 1978). P388 murine leukemia cells (Ramu A. et al. *Cancer Res.,* 43, 5533–7, 1983) were cultured in the presence of increasing amounts of methotroxeate (MET) and doxorubicine (DOX) up to a concentration of $10^{-6}$M. The resulting cell lines were designated P388/MET and P388/DOX respectively.

Cells of the above resistant cell lines were then treated with the following lipid dispersions in saline for 1 hour at room temperature: soy phospholipids (SP); soy phospholipids converted by phospholipase D treatment to >90% phosphatidic acid (PA) and a 1:1 mixture (w/w) of these preparations. The results (shown in Table 4 below) are presented in fluorescence polarization values (P) of 1,3,5 diphenyl hexatriene (DPH) or by the linear scale 2P/(0.46-P) as described in Shinitzki et al. *Biochem. Biophys. Acta.* 515, 367–394, 1978.

TABLE 4

| Cells | P (25° C.)* | 2P (0.46-P) |
|---|---|---|
| P388 (unadapted) | 0.225 ± 0.015 | 1.9 |
| P388/MET | 0.280 ± 0.020 | 3.1 |
| P/388/DOX | 0.285 ± 0.020 | 3.3 |
| P388/MET treated with SP | 0.275 ± 0.030 | 3.0 |
| P388/MET treated with SP | 0.235 ± 0.040 | 2.1 |
| P388/MET treated with PA + SP 1:1 | 0.245 ± 0.035 | 2.3 |
| P388/DOX treated with SP | 0.275 ± 0.040 | 3.0 |
| P388/DOX treated with PA | 0.235 ± 0.025 | 2.1 |
| P388/DOX treated with PA + SP 1:1 | 0.238 ± 0.025 | 2.2 |

*Values are given as mean ± S.D. of 8 different experiments.

The results clearly show that, as previously shown, drug-resistant adapted P388 cells acquire a more rigid membrane than non-treated cells. A short exposure to fluidizing lipids (1 hour), which is relevant for dietary treatment in cancer patients, had only a little effect in combination with SP while treatment of the cells in accordance with the invention with PA and PA+SP was more effective and restored the membrane fluidity almost to the level of unadapted non drug-resistant cells.

EXAMPLE 8
Effect of Treatment with PA or SP on Growth Rates of P388 Cells

P388/MET and P388/DOX resistant cell lines were developed as described in Example 7 above. Non-treated P388 cells and resistant cell lines of these cells were grown in the presence and absence of $10^{-8}$M of MET or DOX as indicated in Table 5 below. The growth rate of each of the above cells was monitored and is shown in the Table.

TABLE 5

| Cells | relative growth rate* |
|---|---|
| P388 (unadapted) | 100 |
| P388 grown in the presence of MET $10^{-8}$M | 10 ± 5 |
| P388 grown in the presence of DOX $10^{-8}$M | 10 ± 5 |
| P388/MET | 100 |
| P388/MET grown in the presence of $10^{-8}$MET | 95 ± 5 |
| P388/MET grown in the presence of $10^{-8}$DOX | 95 ± 5 |
| P388/MET treated with 1 mg/ml SP for 1 hour and then grown in the presence of $10^{-8}$M MET | 85 ± 5 |
| P388/MET treated with 1 mg/ml PA for 1 hour and then grown in the presence of $10^{-8}$MET | 20 ± 5 |
| P388/MET treated with 1 mg/ml PA + SP for 1 hour and then grown in the presence of $10^{-8}$M MET | 25 ± 5 |
| P388/MET treated with 1 mg/ml SP for 1 hour and then grown in the presence of $10^{-8}$M DOX | 90 ± 5 |
| P388/MET treated with 1 mg/ml PA for 1 hour and then grown in the presence of $10^{-8}$M DOX | 20 ± 5 |
| P388/MET treated with 1 mg/ml PA + SP 1:1 for 1 hour and then grown in the presence of $10^{-8}$M DOX | 30 ± 5 |
| P388/DOX | 100 |
| P388/DOX grown in the presence of $10^{-8}$ DOX | 95 ± 5 |
| P388/DOX grown in the presence of $10^{-8}$ MET | 93 ± 5 |
| P388/DOX treated with 1 mg/ml SP for 1 hour and then grown in the presence of $10^{-8}$M DOX | 85 ± 5 |
| P388/DOX treated with 1 mg/ml PA for 1 hour and then grown in the presence of $10^{-8}$M DOX | 20 ± 5 |
| P388/DOX treated with 1 mg/ml PA + SP 1:1 for 1 hour and then grown in the presence of $10^{-8}$M DOX | 24 ± 5 |
| P388/DOX treated with 1 mg/ml SP for 1 hour and then grown in the presence of $10^{-8}$M MET | 90 ± 5 |
| P388/DOX treated with 1 mg/ml PA for 1 hour and then grown in the presence of $10^{-8}$M MET | 20 ± 5 |
| P388/DOX treated with 1 mg/ml PA + SP 1:1 for 1 hour and then grown in the presence of $10^{-8}$M MET | 28 ± 5 | relative growth rate = (percentage growth rate ÷ growth rate of unadapted P388 cells × 100

As clearly shown in this Example, treatment of adapted drug-resistant P388 cells with PA or PA+SP 1:1 restore their sensitivity to either MET or DOX while SP treatment alone, on the other hand, had only a small effect on the cells. It should be noted that the resistance developed in P388/MET cells is also applicable to DOX and vice versa. Similarly, the restoration of susceptibility to drug treatment by PA or PA+SP in P388/MET or P388/DOX cells is non-specific and is applicable to both drugs.

What is claimed is:

1. A method for the treatment of cancer displaying acquired multi-drug resistance, comprising administering to the patient an effective amount of a lipid preparation comprising at least about 10% (w/w) of phosphatidic acid (PA).

2. The method according to claim 1, wherein said lipid preparation is administered in conjunction with a cytotoxic drug.

3. The method according to claim 1, comprising administering to the patient an effective amount of a lipid preparation comprising at least about 20% (w/w) PA.

4. The method according to claim 3, comprising administering to the patient an effective amount of a lipid preparation comprising at least about 50% (w/w) PA.

5. The method according to claim 1, wherein the lipid preparation is obtained by enzymatic treatment of a natural phospholipid preparation with phospholipase-D.

* * * * *